(12) United States Patent
Cheng et al.

(10) Patent No.: US 7,981,527 B2
(45) Date of Patent: Jul. 19, 2011

(54) LIGHT-EMISSION MATERIAL AND ORGANIC LIGHT-EMITTING DIODE INCLUDING THE SAME

(75) Inventors: Chien-Hong Cheng, Hsinchu (TW); Ho-Hsiu Chou, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 124 days.

(21) Appl. No.: 12/492,144

(22) Filed: Jun. 26, 2009

(65) Prior Publication Data

US 2010/0253212 A1  Oct. 7, 2010

(30) Foreign Application Priority Data

Apr. 1, 2009  (TW) .............................. 98110818 A

(51) Int. Cl.
*H01L 51/50*  (2006.01)
(52) U.S. Cl. ........................................ 428/690; 548/414
(58) Field of Classification Search .................. None
See application file for complete search history.

(56) References Cited

U.S. PATENT DOCUMENTS

2009/0167166 A1* 7/2009 Bach et al. ................. 313/504

FOREIGN PATENT DOCUMENTS

JP  2006-104132  * 4/2006

* cited by examiner

*Primary Examiner* — D. Lawrence Tarazano
*Assistant Examiner* — Gregory Clark
(74) *Attorney, Agent, or Firm* — Pai Patent & Trademark Law Firm; Chao-Chang David Pai

(57) ABSTRACT

The invention provides a light-emission material comprising a compound having Formula (I):

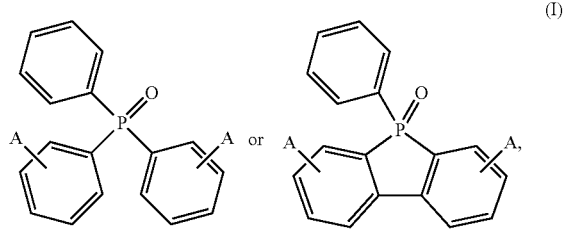

wherein each of A independently is:

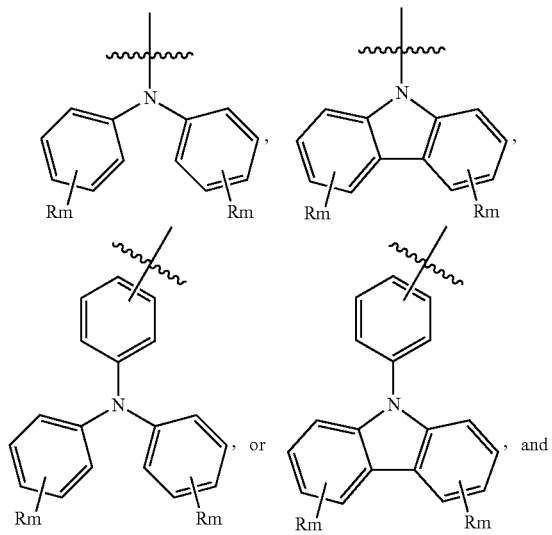

each of Rm independently is H, alkyl, alkenyl, alkynyl, CN, CF3, alkylamino, amino, alkoxy, halo, aryl, or heteroaryl.

20 Claims, 3 Drawing Sheets

LIGHT-EMISSION MATERIAL AND ORGANIC LIGHT-EMITTING DIODE INCLUDING THE SAME

CROSS REFERENCE TO RELATED APPLICATIONS

This Application claims priority of Taiwan Patent Application No. 98110818, filed on Apr. 1, 2009, the entirety of which is incorporated by reference herein.

BACKGROUND OF THE INVENTION

1. Field of the Invention

The present invention relates to a light-emission material for an organic light-emitting diode.

2. Description of the Related Art

An organic light-emitting diode (OLED) (also referred to as organic electroluminescent device) is an LED with an organic layer serving as an active layer. OLEDs have been increasingly applied in flat panel displays due to advantages over other LEDs such as low voltage operation, high brightness, light weight, slim profile, wide viewing angle, and highly effective contrast ratio. The OLED is self-emitting and highly luminous, with wide viewing angles, fast response speeds, and a simple fabrication method.

Generally, OLEDs are composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission. To achieve maximum efficiency of the operation of OLEDs, equilibrium between injecting and transmitting of electrons and holes must be achieved. Thus, it is an important objective for OLEDs to increase combination efficiency of electrons and holes in the light-emission layer. Accordingly, a host-guest system has been disclosed, wherein a light-emission layer doped with a small quantity of a highly efficient light-emission dopant (guest), has been used for increasing combination efficiency of carriers, for required color and sufficient brightness of the fabricated OLEDs. Note that the host delivery carrier does not need to be changed, for the color of the emitting light of the OLED to be the three colors: red, green, and blue, only the light-emission dopant needs to be changed.

Examples of host-quest systems include U.S. Pat. No. 645,645, wherein a phosphorescent OLED having a light-emission layer including a host material of phenanthroline (BCP) and a guest material of fac-tris(2-phenylpyridine)iridium (Ir(ppy)3) used as dopant doped in the host material is disclosed. U.S. Pat. No. 6,097,147 discloses a phosphorescent OLED, wherein, in the light-emission layer, the host material is carbazole biphenyl (CBP) and the guest material is 2,3,7,8,12,13,17,18-o ctaethyl-21H,23H-porphine platinum (II) (PtOEP).

Adachi, in the periodical "Appl. Phys. Lett." (Vol. 78, No. 11, 12 Mar. 2001, pp. 1622-1624) discloses a phosphorescent OLED having a hole-blocker layer, wherein, in the light-emission layer, the host material is CBP and the guest material is iridium bis[2-(2'-benzo[4,5-a]thienyl)pyridinate-N,C.sup.3']acetylacetonate (Btp2Ir(acac)).

Kwong, in the periodical "Appl. Phys. Lett." (Vol. 81, No. 1, 1 Jul. 2002, pp.162-164) discloses a phosphorescent organic light-emitting device having a hole-blocker layer, wherein, in the light-emission layer, the host material is CBP and the guest material is Ir(ppy)3.

In 1999, Forrest discloses in Appl. Phys. Lett. 74, 442 (1999), an organic phosphorescent material, "PtOEP", doped in CBP by evaporation. In 2001, Forrest further discloses in Appl. Phys. Lett. 78, 1622 (2001), a red phosphorescent material containing iridium, "Btp2Ir(acac)", doped in CBP.

BRIEF SUMMARY OF INVENTION

A detailed description is given in the following embodiments with reference to the accompanying drawings.

The invention provides a light-emission material comprising a compound having Formula (I):

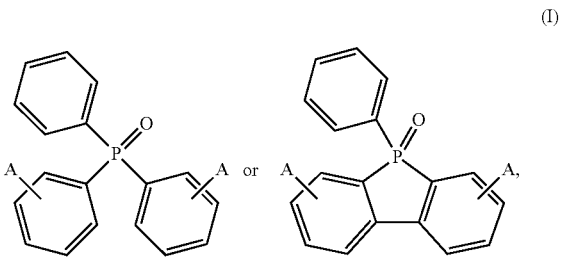

(I)

wherein each of A independently is

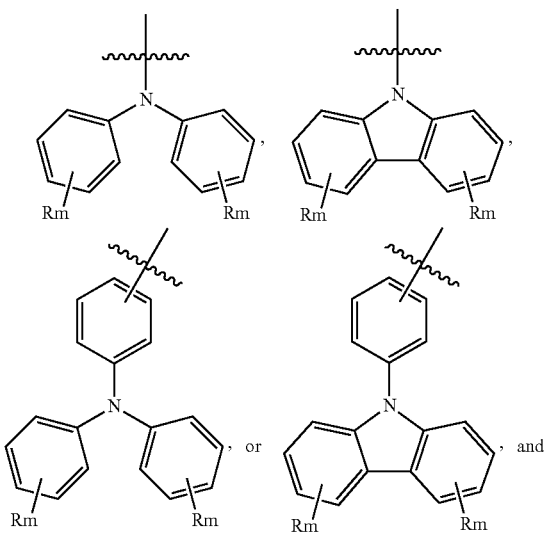

each of Rm independently is H, alkyl, alkenyl, alkynyl, CN, CF3, alkylamino, amino, alkoxy, halo, aryl, or heteroaryl.

The invention provides an organic light-emitting diode, wherein a light-emission layer including the light-emission material having Formula (I), is disposed between a cathode and anode.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

Figure 1:
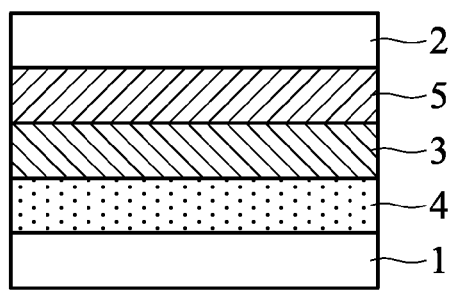
FIGS. 1-3 show organic light-emitting diodes according to embodiments of the present invention.

The present invention provides a light-emission material that can be used for a light-emission layer of an organic light-emitting diode (OLED). The OLED Of the invention has low operating voltage and high efficiency characteristics due to the electron-transporting and hole-transporting characteristics of the light-emission material. The light-emission material includes a compound that can be used for a host material of the light-emission layer, having Formula (I)

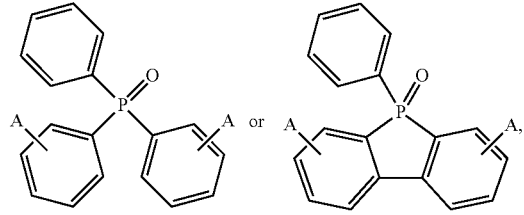
(I)

wherein each of A independently is

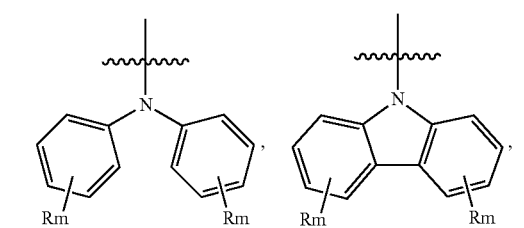

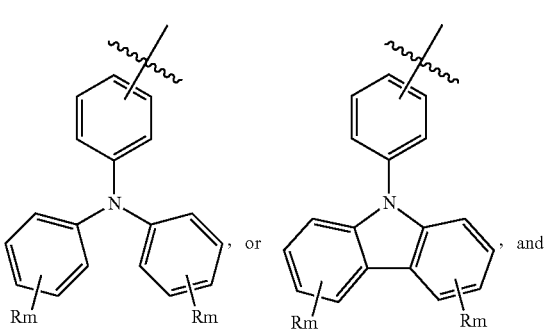

each of Rm independently is H, alkyl, alkenyl, alkynyl, CN, CF3, alkylamino, amino, alkoxy, halo, aryl, or heteroaryl.

A are preferably the same. Rm are preferably the same.

Representative examples of the light-emission compound conforming to the described definition include, but are not limited to:

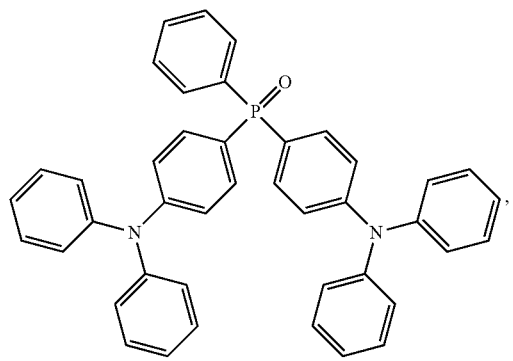

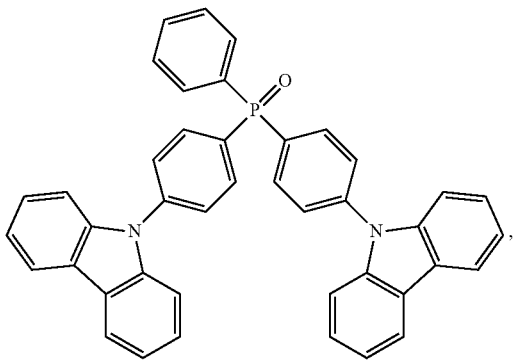

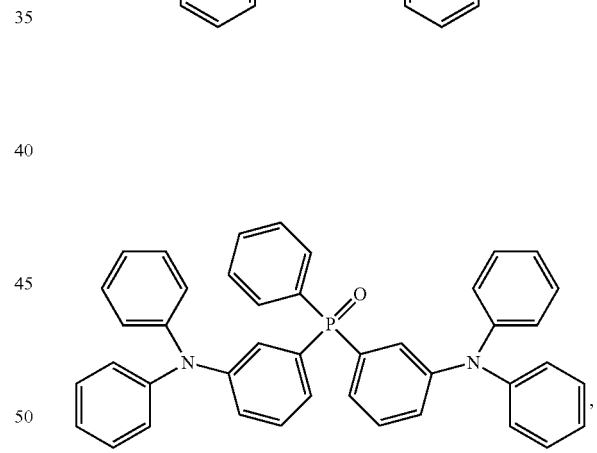

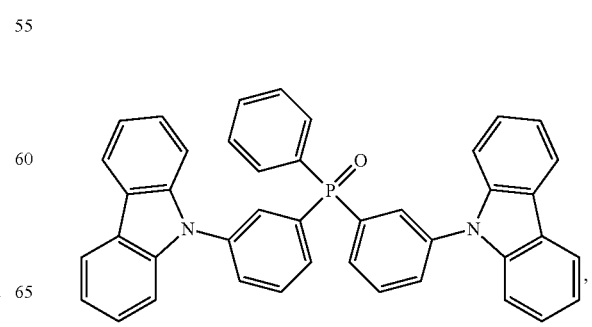

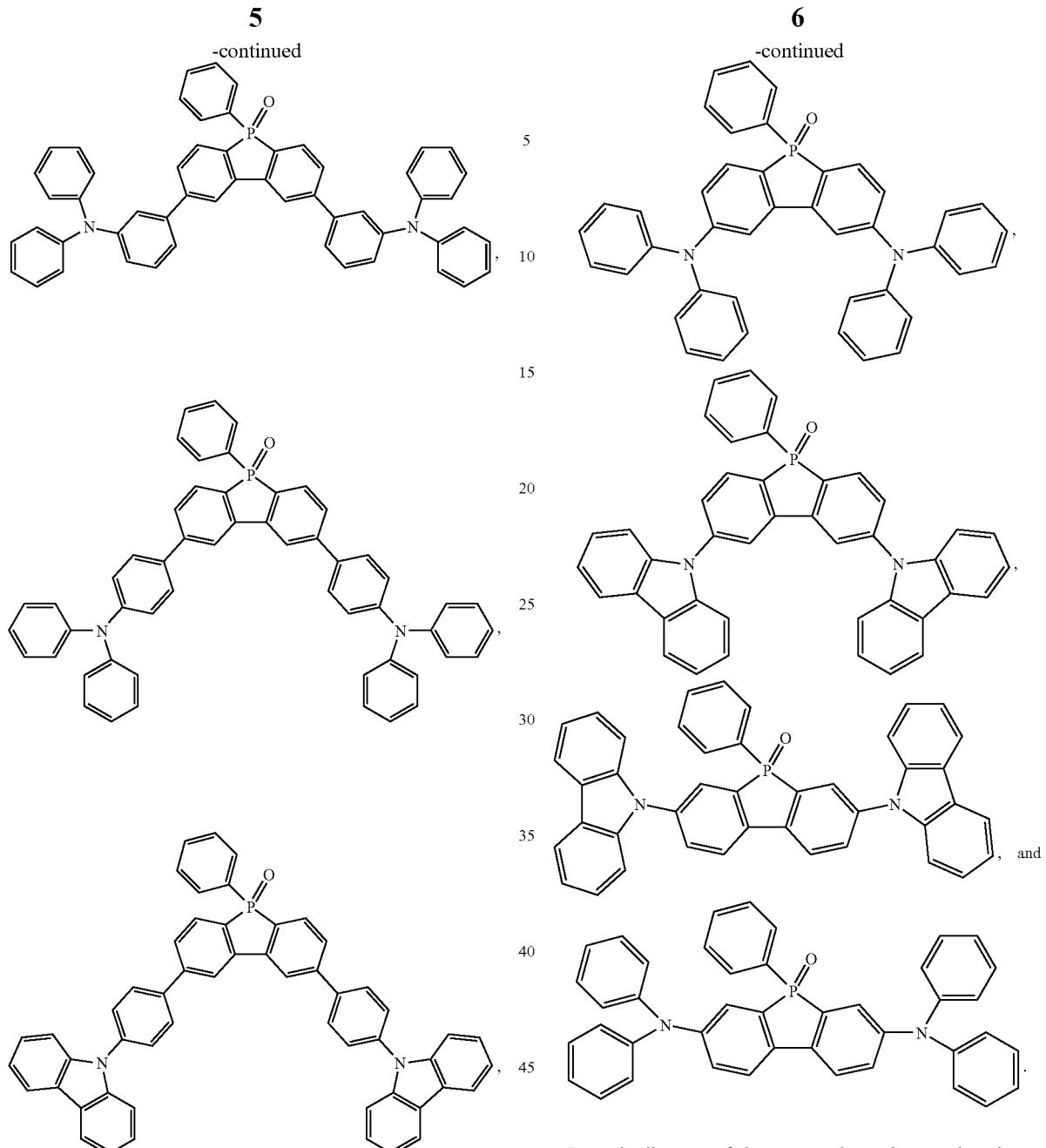
In embodiments of the present invention, a phosphorescence-emission material may be formed by doping (or co-doping) a guest material such as phosphorescent organometallic complex into the host material of the invention by a vacuum deposition method. The guest material may have Formula (II):
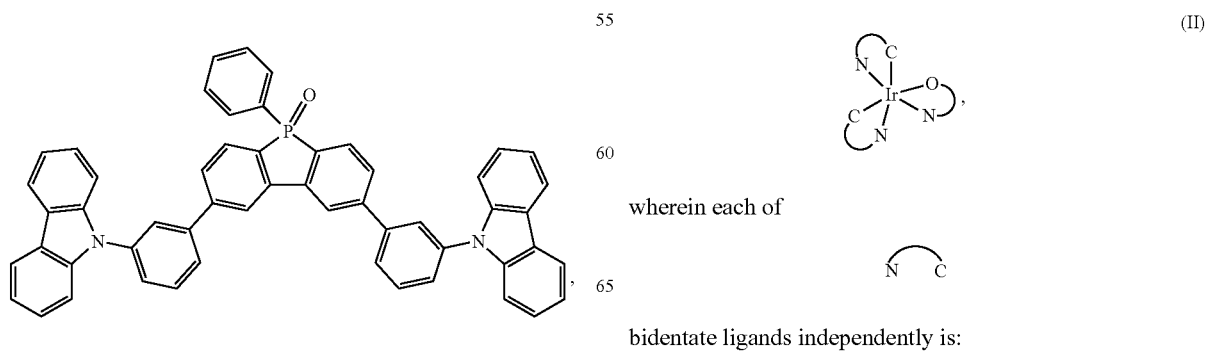
wherein each of
bidentate ligands independently is:

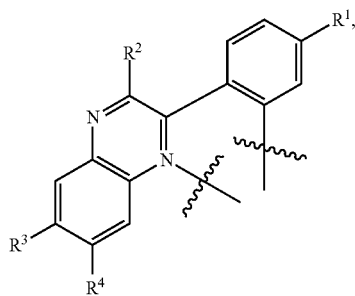
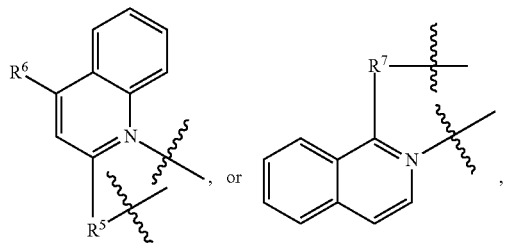
a
bidentate ligand is:
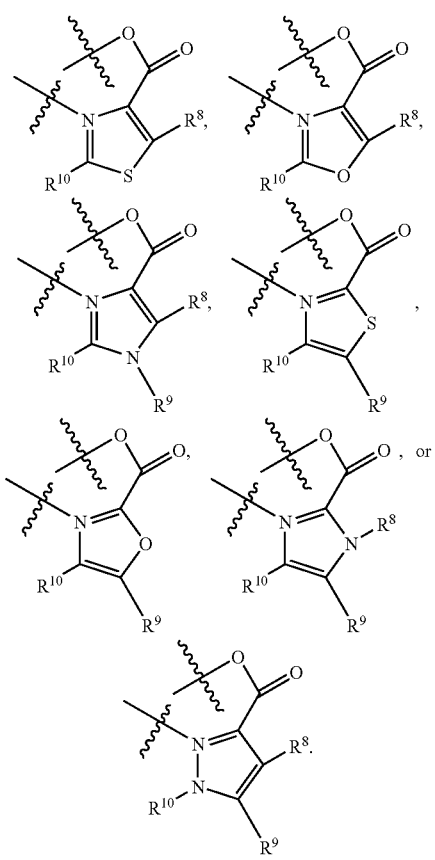
R1 to R10 each independently are H, alkyl, alkenyl, alkynyl, CN, CF3, alkylamino, amino, alkoxy, halo, aryl, or heteroaryl.
R1 preferably is H or F. R3 and R4 preferably are the same.
In some specific embodiments, the
bidentate ligands are the same, and include the following:
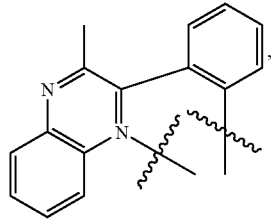
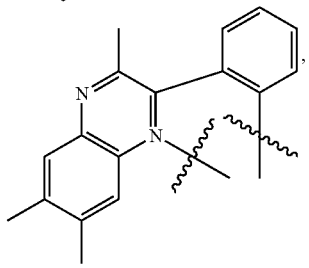
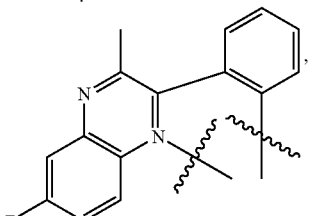
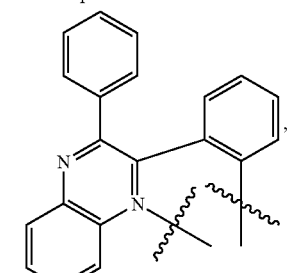
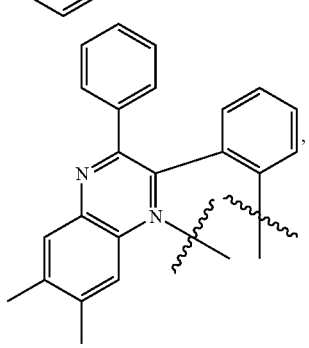

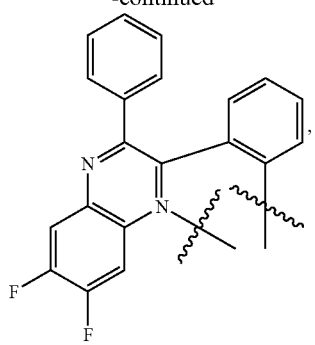
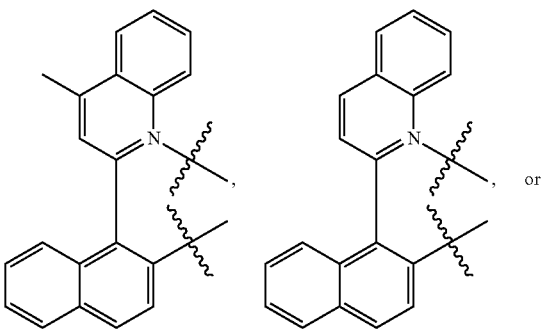
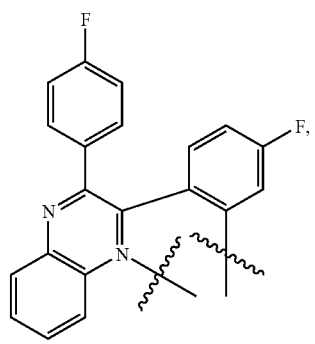
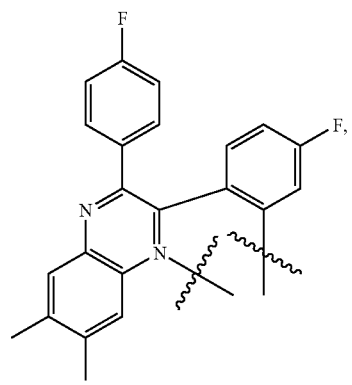
In some specific embodiments,
bidentate ligand is:
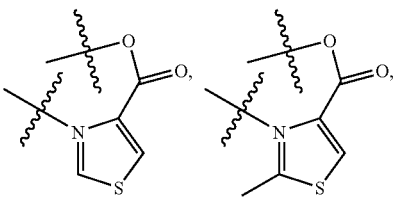
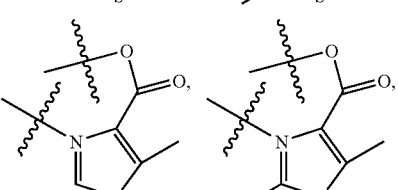
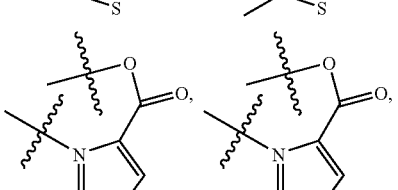
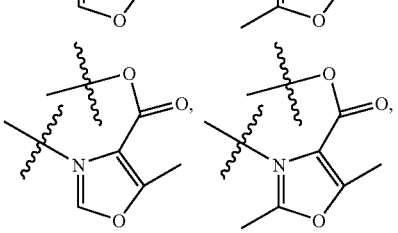

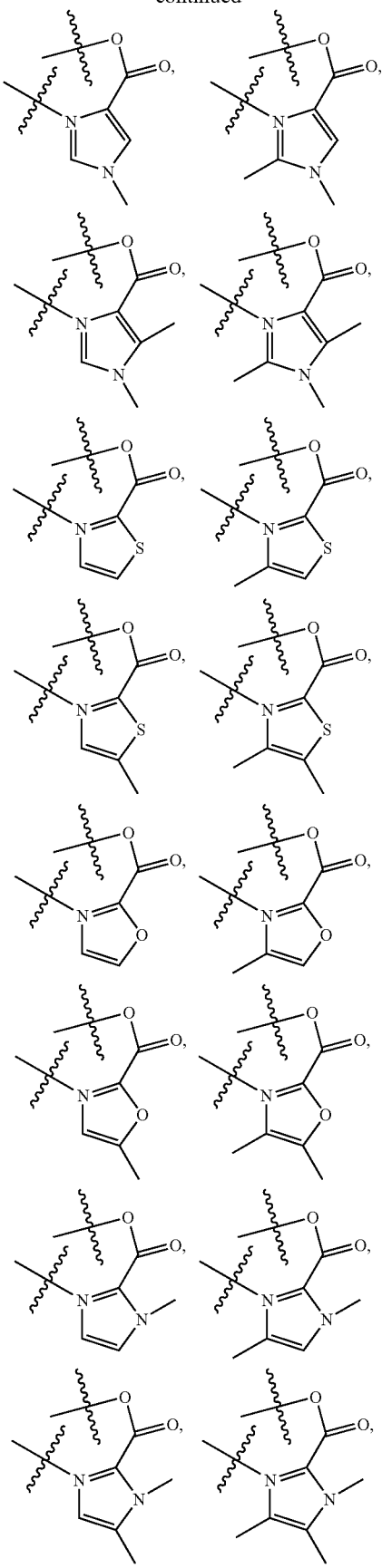
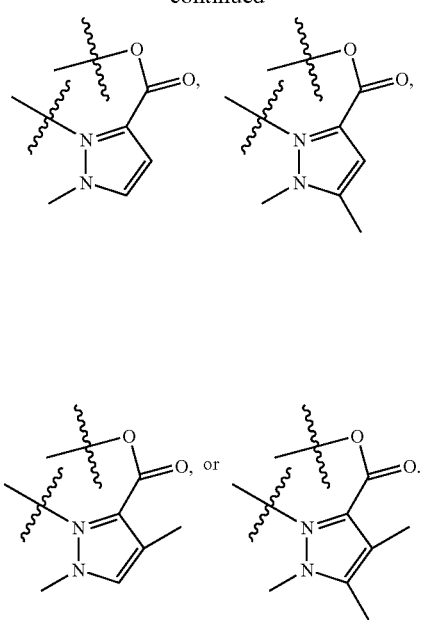
Representative examples of the phosphorescent organometallic complex guest materials include, but are not limited to:
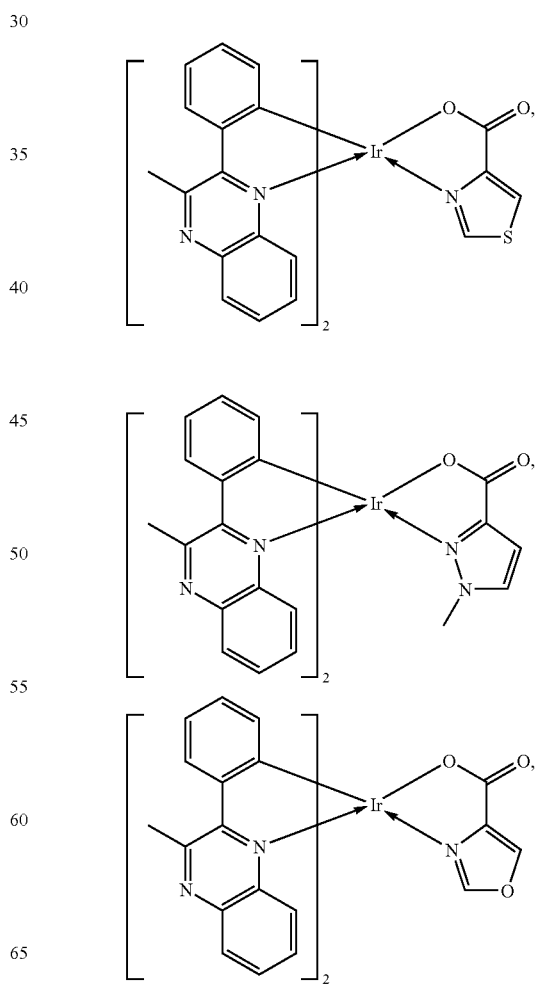

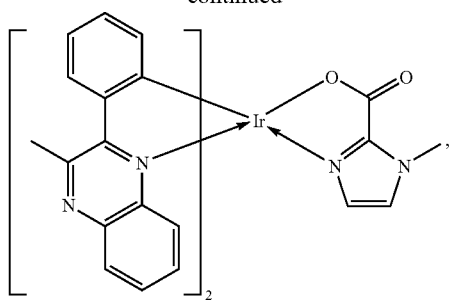
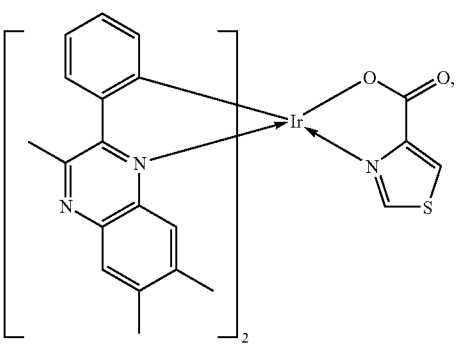
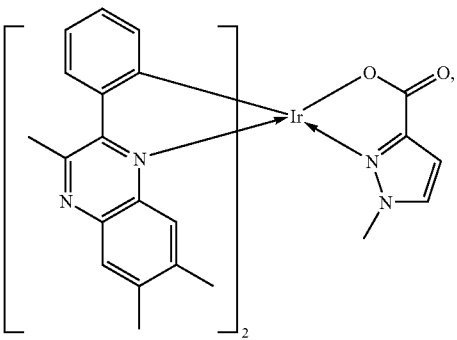
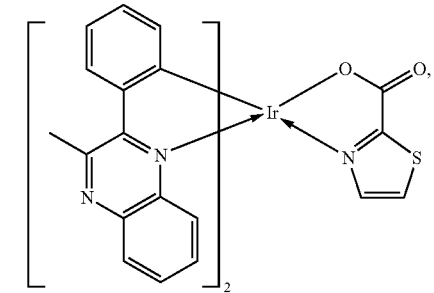
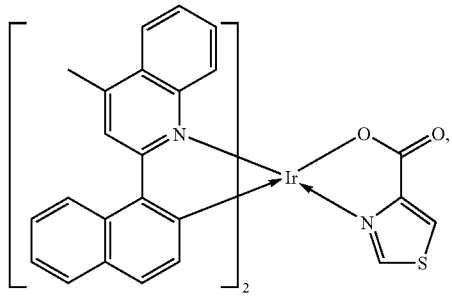
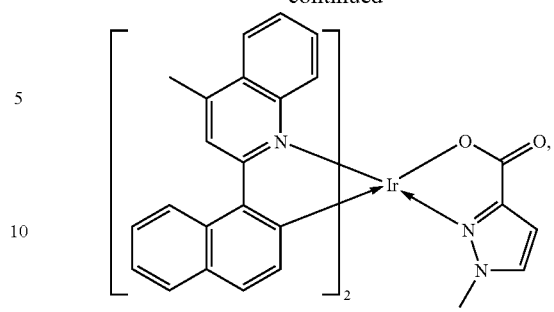
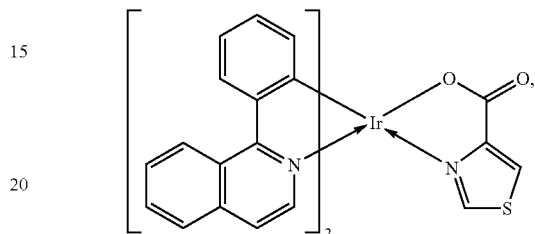
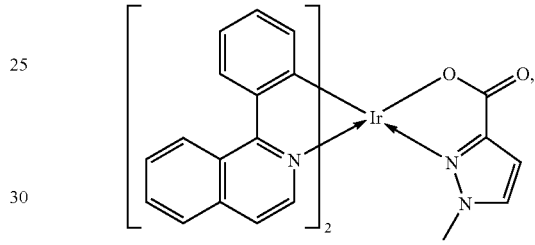
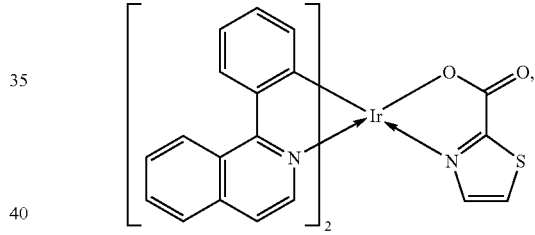
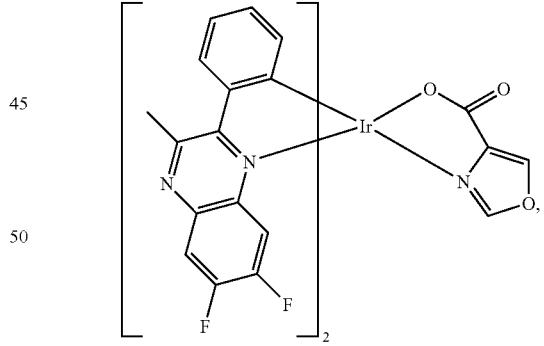
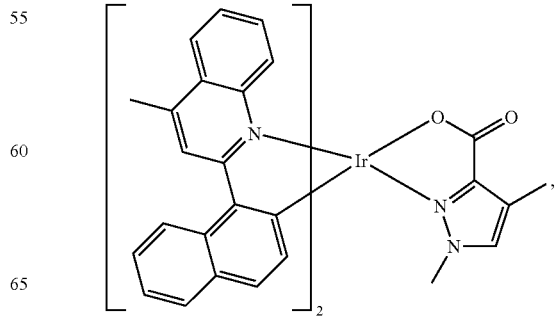

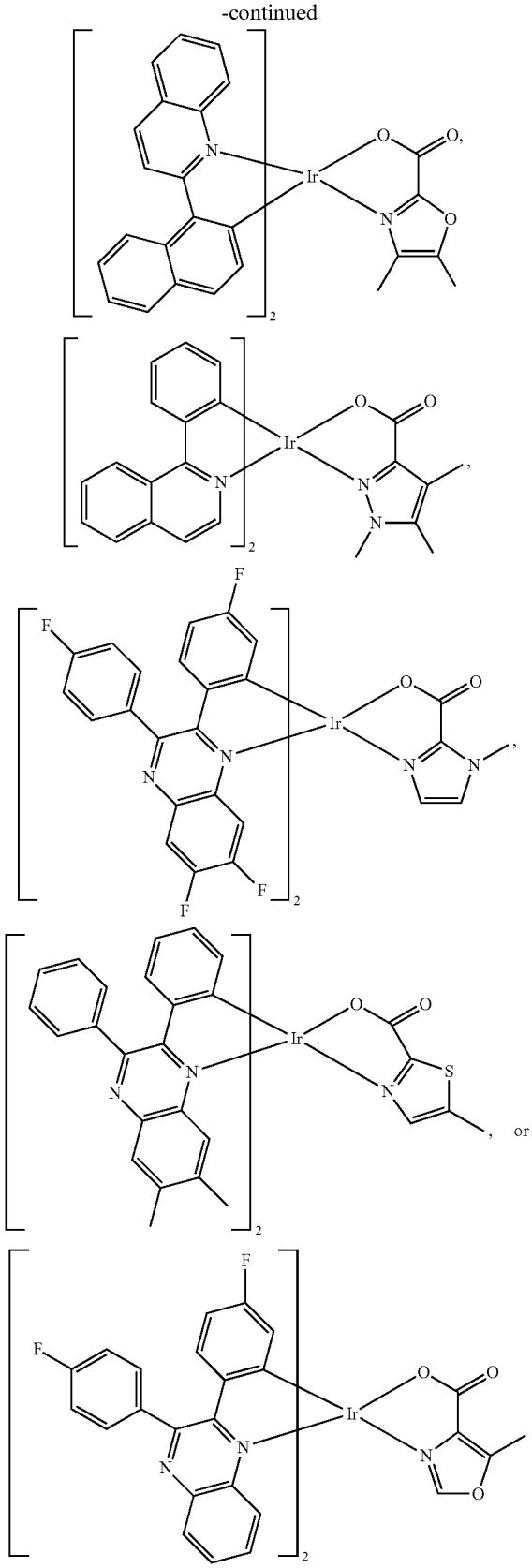

In embodiments, the guest materials are red phosphorescent materials. Therefore, the red phosphorescence-emission material can be formed by doping the red phosphorescent guest material into the host material.

It should be noted that the guests of the light-emission material of the present invention are not limited to the compounds described above. Other conventional materials can be used for forming light-emission materials for varied purposes. The conventional materials comprise materials disclosed in the published references such as US 2002024293, US 2002034656, US 2002045061, US 2003017361, US 2003092935, US 2003102800, US 2004053071, US 2004102632, US 2004086743, US 2004110031, JP 2002226495, JP 2002338588, JP 2003109758, JP 2003113246, JP 2003119179, JP 2003123982, JP 2003147021, JP 2003171391, JP 2003206320, JP 2003253128, JP 2003253129, JP 2003253145, JP 2004111379, WO 2004026886, WO 2004028217, WO 2004037836, WO 2004048395, and WO 2004055130.

The light-emission material of the present invention is used for emitting light. The dopant and the doping quantity of the light-emission material can be varied according to the organic electro-luminescence material used and required device characteristics. Therefore, the present invention is not limited to the doping quantity of the dapant described herein.

Figure 2:
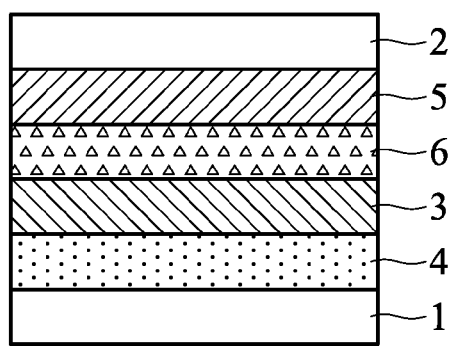
Figure 3:
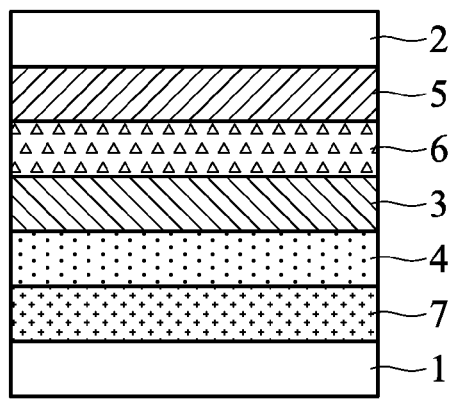

FIGS. 1-3 show organic light-emitting diodes, particularly red phosphorescent organic light-emitting diodes, according to embodiments of the present invention. The light-emission layer 3 including the organometallic complex of the invention is disposed between an anode 1 and a cathode 2. In embodiments, the host compound is formed by the vacuum deposition method for forming the light-emission layer 3. Alternatively, the guest metallic iridium complex is doped (or co-doped) into the host material by the vacuum deposition method for forming the light-emission layer 3.

The anode 1 or cathode 2 includes, but is not limited to, indium tin oxide (ITO), indium zinc oxide (IZO), aluminum zinc oxide (AZO), zinc oxide (ZnO), $SnO_2$, $In_2O_3$, Al, Cu, Mo, Ti, Pt, Ir, Ni, Cr, Ag, Au, or combinations thereof. The anode 1 or cathode 2 may be formed by the method including, but is not limited to, sputtering, electron beam evaporation, thermal evaporation, or chemical vapor deposition.

Between the anode 1 and the cathode 2 shown in FIG. 1, a hole-transport layer 4, a light-emission layer 3, and an electron-transport layer 5 are sequentially disposed on the anode 1. In FIG. 2, the hole-transport layer 4, the light-emission layer 3, a hole-blocker layer 6, and the electron-transport layer 5 are sequentially disposed on the anode 1. In FIG. 2, the hole-blocker layer 6 is inserted between the light-emission layer 3 and electron-transport layer 5, which is different from FIG. 1. In FIG. 3, the hole-transport layer 4, an electron-blocker layer 7, the light-emission layer 3, the hole-blocker layer 6, and the electron-transport layer 5 are sequentially disposed on the anode 1. In FIG. 3, the electron-blocker layer 7 is inserted between the anode 1 and hole-transport layer 4, which is different from FIG. 2.

The hole-transport layer 4 includes, but is not limited to, N,N'-bis(naphthalene-1-yl)-N,N'-bis(phenyl)-benzidine (NPB), N,N,N',N'-Tetrakis(naphth-2-yl)benzidine (TNB; NT2). The electron-transport layer 5 includes, but is not limited to, 4,7-diphenyl-1,10-phenathroline (BPhen), 2,9-dimethyl-4,7-diphenyl-1,10-phenathroline (BCP), 2,2',2"-(1,3,5-benzinetriyl)-tris(1-phenyl-1-H-benzimidazole) (TBPI), tris(8-hydroxyquinoline)aluminum (Alq3). The hole-blocker layer 6 includes, but is not limited to, 4,7-diphenyl-1,10-phenathroline (BPhen), 2,9-dimethyl-4,7-diphenyl-1,10-phenanthroline (BCP), (III)bis(2-methyl-8-quinolinato)4-phenyl-phenolato)aluminum(III) (BAlq), 1,3,5-tris(phenyl-2-benzimidazolyl)-benzene (TPBI), aluminium (III) bis(2-methyl-8-quninolinato)-phenolate (PAlq), aluminium (III) bis(2-methyl-8-quninolinato)-triphenylsilanyloxy (SAlq), or 1,4-bis(triphenylsilyl)benzene (UGH2). The electron-blocker layer 7 includes, but is not limited to, an alkali metal halide, alkali earth metal halide, alkaline metal oxide, or metal carbonate, such as LiF, CsF, NaF, $CaF_2$, $Li_2O$, $Cs_2O$, $Na_2O$, $Li_2CO_3$, $Cs_2CO_3$ or $Na_2CO_3$.

Note that the formation methods the hole-transport layer 4, electron-transport layer 5, hole-blocker layer 6, and electron-blocker layer 7 are not limited, and can be conventional methods such as thermal vacuum evaporation, spin coating, immersion coating, rolling coating, ink refilling, embossing, impression, physical vapor deposition, or chemical vapor deposition. Moreover, the arrangement of the films of the invention is not limited to the structure shown in FIGS. 1-3. The arrangement of the films can be varied depending on desired device characteristics.

The following description is of the best-contemplated mode of carrying out the invention. This description is made for the purpose of illustrating the general principles of the invention and should not be taken in a limiting sense. The scope of the invention is best determined by reference to the appended claims.

Example 1

Synthesis of the APOA

The reaction according to Example 1 is shown as below:

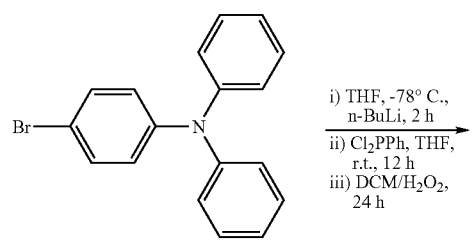

i) THF, -78° C., n-BuLi, 2 h
ii) $Cl_2$PPh, THF, r.t., 12 h
iii) $DCM/H_2O_2$, 24 h

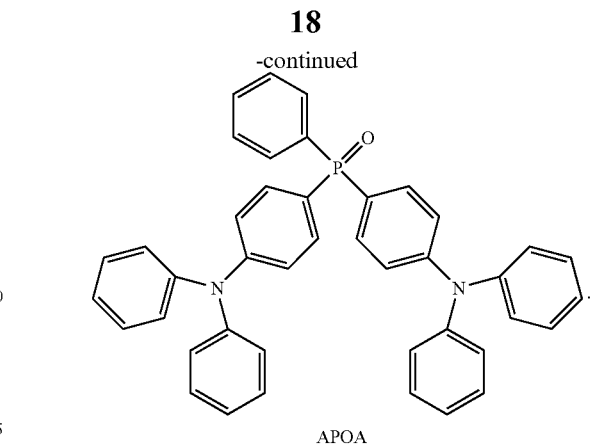

APOA 4-bromotriphenylamine (2 mmol) was put into a round-bottom flask, and dissolved by introducing tetrahydrofuran (20 mL). The temperature of the mixture was lowered to -78° C. by using dry ice and acetone, and n-butyllithium (2.1 mmol, 2.5M) was added and the added mixture was left standing for 2 hours. Then, dichlorophenyl phosphine (1 mmol) was put into another round-bottom flask and dissolved by introducing tetrahydrofuran (10 mL), and then the dissolved mixture was introduced into the prior round-bottom flask with 4-bromotriphenylamine by using a transfer needle. Then, the temperature of the combined mixture was allowed to change to room temperature and then stirred for 12 hours. After the reaction, an un-oxidized solid was got by extracting by using dichloromethane, ridding of water by using magnesium sulfate after gathering the organic layer, and purifying by the column chromatography. Then, the purified solid was dissolved in dichloromethane and hydrogen peroxide of 30% (1:1), and stirred for 24 hours. Next, the dissolved solid was dried by a rotary evaporator and further purified by a sublimator, to obtain a white-colored product with a yield of 65%.

Spectrum Data of the APOA:

$^1$H NMR (400 MHz, CDCl3, ppm): δ7.002-7.028 (4H, m,), 7.073-7.137 (11H, m), 7.257-7.305 (9H, m), 7.413-7.513 (7H, m), 7.687-7.738 (4H, m)

Figure 4:
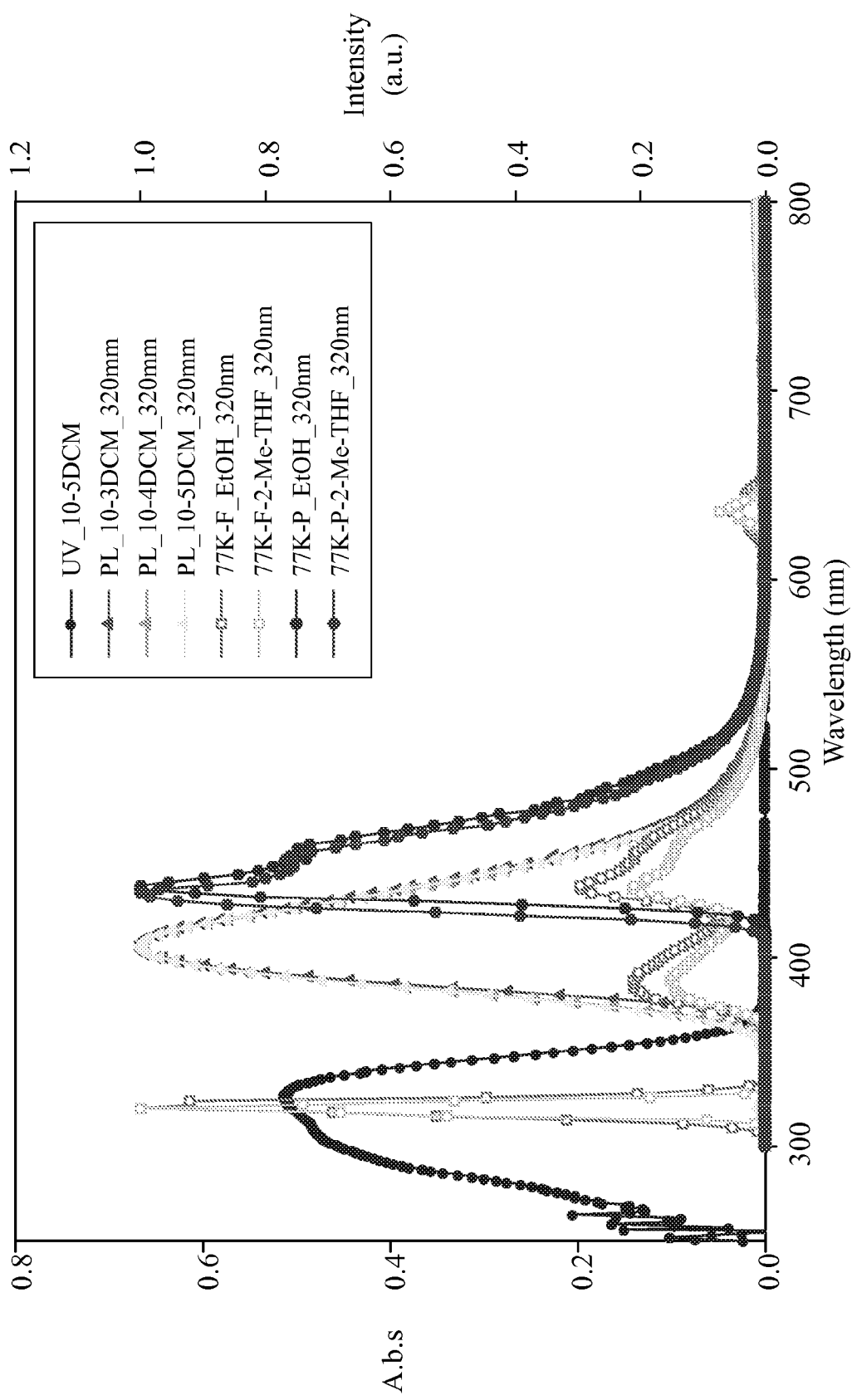
FIG. 4 shows a spectrogram of the APOA of one embodiment of the present invention.

The product (APOA) obtained from Example 1 was tested. FIG. 4 shows a spectrogram of UV absorption (dissolved in DCM, 10-5M), phosphorescence (dissolved in DCM, $10^{-3}$M, $10^{-4}$M, $10^{-5}$M), low temperature fluorescence and phosphorescence (dissolved in Me-THF or EtOH, 77K) of the APOA. The photophysical characteristics of the APOA are shown in Table 1.

|  | λmax Abs. in DCM (nm) | λmax FL in DCM (nm) | λmax FL (77 K) (nm) | λmax FL (77 K) (nm) | HOMO (eV) | Es (eV) | ET (eV) |
|---|---|---|---|---|---|---|---|
| APOA | 326 ($10^{-5}$ M) | 406 ($10^{-3}$ M) 406 ($10^{-4}$ M) 406 ($10^{-5}$ M) | 388 | 436 | 5.52 | 3.44 | 2.85 | p.s.
the solvent used in 77 K test is Me-THF

As shown in FIG. 4 and Table 1, the maximum UV absorption of the APOA dissolved in dichloromethane was 326 nm. In the FL spectrogram shown in FIG. 4, the light-emitting position of the APOA dissolving in dichloromethane was about 406 nm. Meanwhile, as the APOA concentration increased, the light-emitting position of the red color slightly shifted. Moreover, the singlet gap (Es) of the APOA was 3.44 eV, calculated by using the intersection point of the UV-Vis absorption spectrogram and the FL spectrogram.

Note that for fabrication, to optimize a device efficiency, the triplet gap of the phosphorescent host material should match the guest material. The triplet gap can be obtained by using a phosphorescence spectrogram at the low temperature of 77K. The triplet gap of the APOA was 2.85 eV, obtained by using the low-temperature phosphorescence spectrogram tested with Me-THF.

Example 2

Synthesis of the APPOPA

The reaction is shown as below:

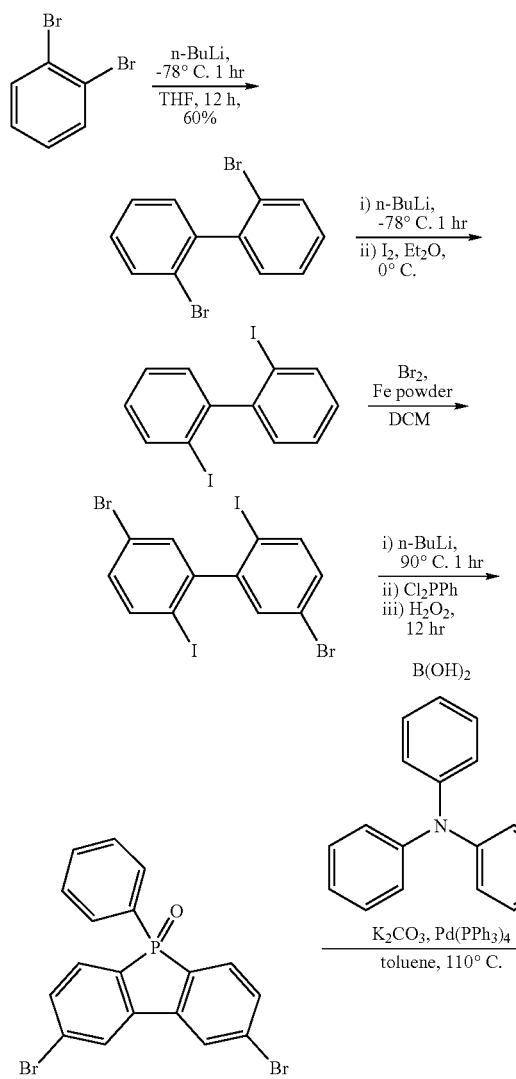

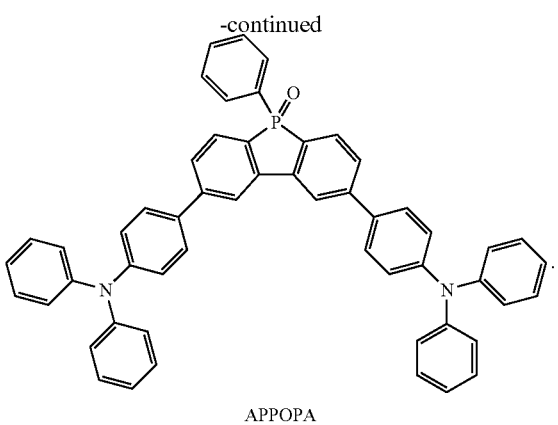

APPOPA

Step 1

Synthesis of 2,2'-dibromobiphenyl

The reaction is shown as below:

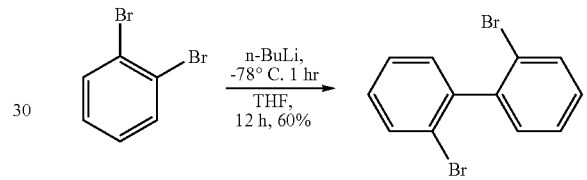

1,2-dibromobenzene (7.5 g, 31.8 mmole) was put into a reaction flask. Then, under nitrogen gas, the mixture was dried using THF (75 mL) as a solvent. n-Butyllithium (6.68 mL, 16.7 mmole) was slowly introduced into the reaction flask at a temperature of −78° C. over 1 hour. After allowed to cool to room temperature, the reacted mixture was stirred for 12 hours. The organic layer was obtained by extracting with water and ether, and ridded of water by using anhydrous magnesium sulfate. 2,2'-dibromobiphenyl, yield of 60%, was obtained by the purification with n-hexane after the condensing. The spectrum data of the 2,2'-dibromobiphenyl was the same as the spectrum data of the reference (K. L. Chan, S. E. Watkins, Chris S. K. Mak, M. J. McKiernan, Carl R. Towns, S. I. Pascu, A. B. Holmes, Chem Comm, (2005)).

Spectrum Data of 2,2'-dibromobiphenyl:
$^1$H NMR (400 MHz, CDCl3, ppm): δ7.24 (1H, m, ArH), 7.28 (1H, m, ArH), 7.37 (1H, dd, J 7.8 1.2 ArH), 7.67 (1H, dd, J 7.5 0.8 ArH)

Step 2

Synthesis of 2,2'-diiodobiphenyl

The reaction is shown as below:

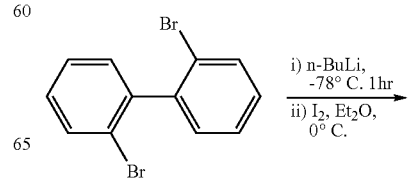

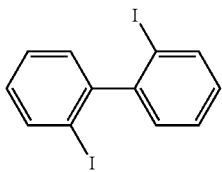

2,2'-dibromobiphenyl (7 g, 22 mmole) was put into a reaction flask. The reaction flask was filled with nitrogen gas after a pumping vacuum and heating. Then, ether (35 mL) used as a solvent was introduced into the heated mixture. n-Butyllithium (20 mL, 50 mmole) was slowly introduced into the reacted mixture at a temperature of −78° C. over 1 hour. After allowed to adjust to room temperature, the mixture was stirred for 12 hours. An iodine ether solution (iodine 12.6 g, 50 mmole; ether, 52 mL) was dripped into the mixture in an ice bath. Then, after allowed to adjust to room temperature, the mixture was stirred for over 2 hours. Next a saturated sodium thiosulfate solution was added to the mixture. The organic layer was gathered after extracting with water, and ridded of water by using anhydrous magnesium sulfate. A 2,2'-diiodobiphenyl, with a yield of 78%, was obtained following condensation and purification with n-hexane. The spectrum data of the obtained 2,2'-diiodobiphenyl was the same as with the spectrum date of the reference (K. L. Chan, S. E. Watkins, Chris S. K. Mak, M. J. McKieman, Carl R. Towns, S. I. Pascu, A. B. Holmes, Chem Comm, (2005)).

Spectrum Data of 2,2'-diiodobiphenyl $^1$H NMR (400 MHz, CDCl3,ppm): δ7.10 (2H, ddd, J8.0 7.6 1.7, ArH), 7.20 (2H, dd, J 7.6 1.7, ArH), 7.44 (2H, ddd, J 7.6 7.6 1.1, ArH), 7.96 (2H, dd, J 8.0 1.1, ArH)

Step 3

Synthesis of 5,5'-dibromo-2,2'-diiodobiphenyl

The reaction is shown as below:

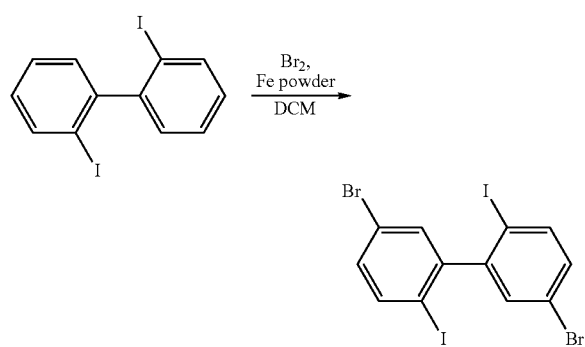

2,2'-diiodobiphenyl (0.5 g, 1.23 mmole) and ion powder (0.01 g, 0.179 mmole) was put into a round-bottom flask. DCM (10 mL) in a nitrogen gas after a pumping vacuum and heating. The solution was heated to 50° C. and stirred for 12 hours after slowly adding bromine 0.252 mL. The reaction was completely finished by the saturated sodium thiosulfate solution. The organic layer was gathered after extracting with DCM, and ridded of water by using anhydrous magnesium sulfate. The more purified 5,5'-dibromo-2,2'-diiodobiphenyl, yield of 40%, was obtained by the purification with DCM after the condensing. The spectrum data of obtained 5,5'-dibromo-2,2'-diiodobiphenyl was the same spectrum data of the reference (K. L. Chan, S. E. Watkins, Chris S. K. Mak, M. J. McKiernan, Carl R. Towns, S. I. Pascu, A. B. Holmes, Chem Comm, (2005)).

Spectrum data of 5,5'-dibromo-2,2'-diiodobiphenyl $^1$H NMR (400 MHz, CDCl3, ppm): δ7.24 (2H, dd, J8.4 2.3, ArH), 7.32 (2H, d, J 2.3, ArH), 7.78 (2H, d, J8.4, ArH)

Step 4

Synthesis of 3,6-Dibromo-9-phenyl-9-phosphafluorene Oxide

The reaction is shown as below:

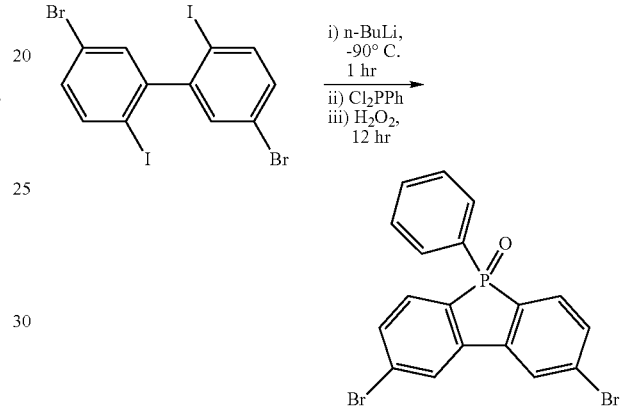

5,5'-dibromo-2,2'-diiodobiphenyl (0.5638 g, 1 mmole) was put in a two-neck reaction bottle. THF (10 mL) was put in the reaction bottle after heating the reaction bottle. n-Butyllithium (0.84 mL, 2.1 mmole) was slowly introduced into the reaction bottle over 1 hour after cooling down to below −90° C. Next, the solution was stirred for 30 minutes with the maintaining temperature. Next, Cl2PPh (0.2 g, 1.1 mmole) was added into the solution. The solution was stirred for 12 hours after turning back to the room temperature. The organic layer was obtained by extracting with water and ether, and ridded of water by using anhydrous magnesium sulfate. The un-oxidized compound 4 was obtained by the column chromatography with n-hexane after the condensing. The compound 4 was added with 10 mL DCM, stirred for 12 hours with 10 mL hydrogen peroxide, and poured into the separatory funnel for extract the organic layer. 3,6-Dibromo-9-phenyl-9-phosphafluorene oxide was obtained after the condensing by ridding of water with anhydrous magnesium sulfate.

Spectrum data of 3,6-Dibromo-9-phenyl-9-phosphafluorene oxide $^1$H NMR (400 MHz, CDCl$_3$, ppm): δ 7.387~7.399 (2H, m), 7.481~7.610 (7H, m), 7.924 (2H, s)

$^{13}$C NMR (100 M Hz, CDCl$_3$): δ 119.25 (CH, d, J=44 Hz), 123.36 (CH), 124.75 (CH), 127.79 (CH), 128.00 (CH), 128.73 (CH, d, 52 Hz), 129.37 (CH), 130.22 (CH, d, J=40 Hz), 130.67 (C), 131.11 (CH, d, J=44 Hz), 131.75 (CH), 132.09 (C), 133.43 (C), 142.33 (C), 142.54 (C), 146.01 (C), 147.40 (C), 148.27 (C).

HRMS (FAB, m/z): calcd for C18H11Br2OP 431.89, found 431.8922.

Step 5

Synthesis of the APPOPA

The reaction is shown as below:

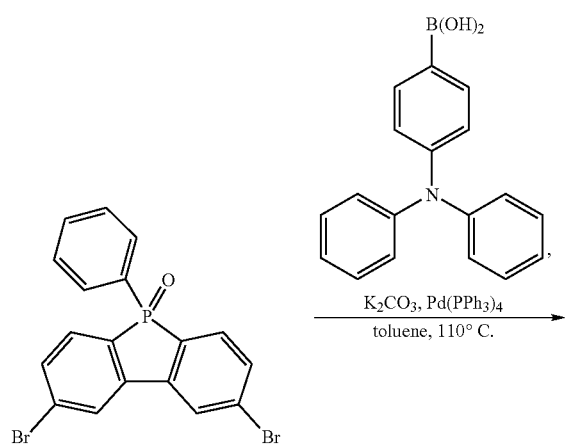

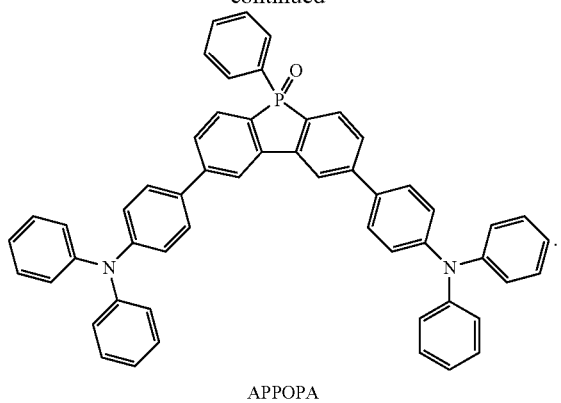

APPOPA 3,6-Dibromo-9-phenyl-9-phosphafluorene oxide (0.108 g, 0.25 mmole), nitrogen-comprising borate (0.181 g, 0.625 mmole), potassium carbonate (0.138 g, 1 mmole), and Pd(PPh3)4 catalytic agent (0.015 g, 0.0125 mmole) were put into a two-neck reaction bottle. 1.5 mL of toluene under nitrogen gas was added to the mixture, heated to 110° C. and stirred for 24 hours. Following, 5 mL of toluene was added to the reacted mixture APPOPA was obtained after extracting with 10 mL of water, and water was extracted by using anhydrous magnesium sulfate, condensing, and sublimating.

Spectrum Data of the APPOPA:

$^1$H NMR (400MHz, CDCl3,ppm): δ 7.034~7.069 (4H, m), 7.129~7.161 (12H, m), 7.242~7.294 (8H, m), 7.400~7.413 (2H, m), 7.473~7.576 (7H, m), 7.683~7.768 (4H, m), 8.039 (2H, s)

$^{13}$C NMR (100 M Hz, CDCl3): δ 144.89 (CH, d, J=41.2 Hz), 128.68 (C, d, J=11.6 Hz), 128.92 (CH, d, J=52.8 Hz), 130.91 (CH, d, J=44 Hz), 131.21 (CH, d, J=40.8), 131.44 (C), 132.506 (C), 132.62 (CH, d, J=12Hz), 133.09 (CH, d, J=48 Hz), 142.30 (C, d, J=88 Hz).

HRMS (FAB, m/z): calcd for C54H39N2OP 762.2800, found 762.2798.

Figure 5:
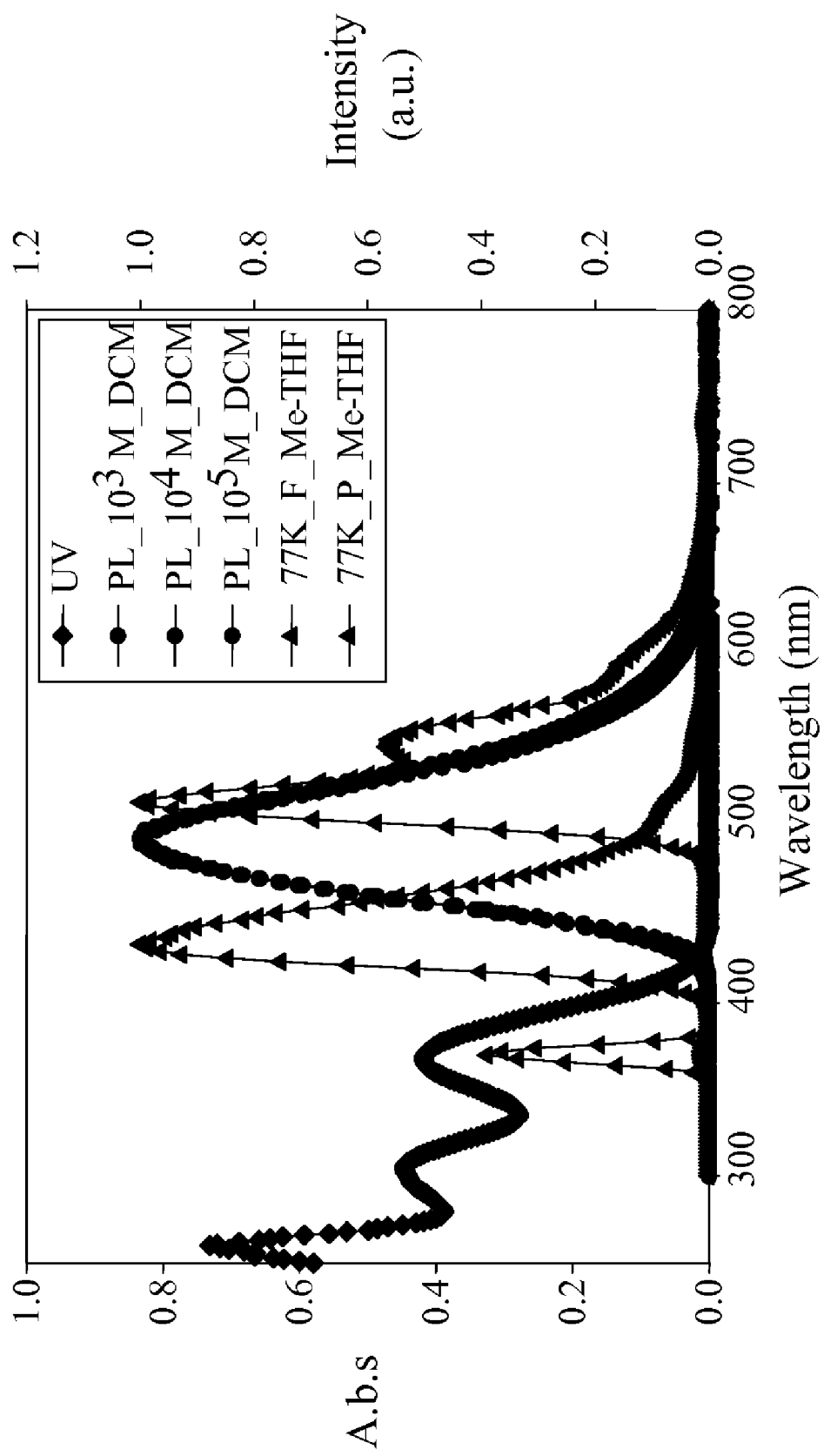
FIG. 5 shows a spectrogram of the APPOPA of one embodiment of the present invention.

The product (APPOPA) obtained from Example 2 was tested. FIG. 5 shows a spectrogram of the UV absorption, phosphorescence (dissolved in DCM, 10-3M, 10-4M, 10-5M), low temperature fluorescence and phosphorescence (dissolved in Me-THF or EtOH, 77K) of the APPOPA. The photophysical characteristics of the APPOPA are shown in Table 2.

|  | λmax Abs. in DCM (nm) | λmax FL in DCM (nm) | λmax FL (77 K) (nm) | λmax FL (77 K) (nm) | HOMO (eV) | Es (eV) | ET (eV) |
|---|---|---|---|---|---|---|---|
| APPOPA | 260; 305; 368 ($10^{-5}$ M) | 496 ($10^{-3}$ M) 496 ($10^{-4}$ M) 494 ($10^{-5}$ M) | 434 | 516 | 5.41 | 2.94 | 2.41 |

As shown in FIG. 5 and Table 2, the UV absorption range of the APPOPA dissolved in dichloromethane was 260-370 nm. In the FL spectrogram shown in FIG. 5, the light-emitting position of the APPOPA dissolving in dichloromethane was about 494-496 nm. Meanwhile, as the APPOPA concentration increased, the light-emitting position of the red color slightly shifted. Moreover, the singlet gap (Es) of the APPOPA was 2.94 eV, calculated by using the intersection point of UV-Vis absorption spectrogram and the FL spectrogram.

Note that for fabrication, to optimize a device efficiency, the triplet gap of the phosphorescent host material should match the guest material. The triplet gap can be obtained by using a phosphorescence spectrogram at the low temperature of 77K. The triplet gap of the APPOPA was 2.41 eV, obtained by using the low-temperature phosphorescence spectrogram tested with Me-THF.

Example 3

Synthesis of the CPOC

The reaction is shown as below:

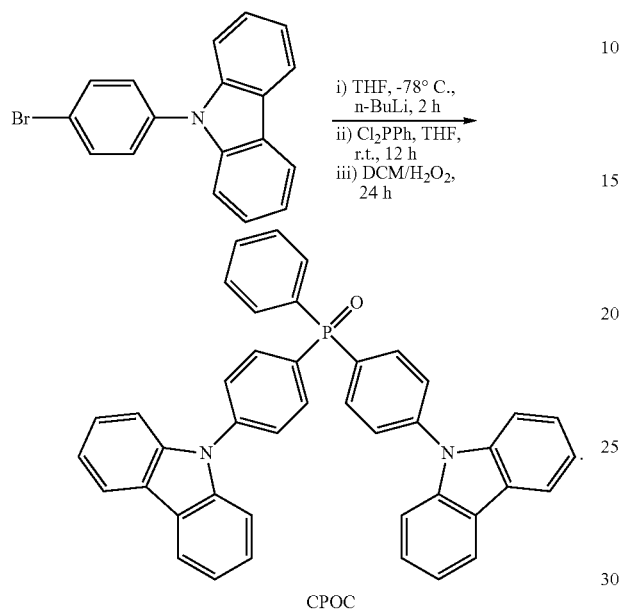

CPOC 9-(4-bromophenyl)-9H-carbazole (2 mmol) was put in a round-bottom flask, and dissolved by introducing tetrahydrofuran (20 mL). The round-bottom flask was at the temperature of −78° C. by using dry ice and acetone, and kept the temperature for 2 hours after introducing n-butyllithium (2.1 mmol, 2.5M). Then, dichlorophenyl phosphine (1 mmol) was put in the other round-bottom flask and dissolved by introducing tetrahydrofuran (10 mL), and then introduced into the prior round-bottom flask by using a transfer needle. Then, the round-bottom flask was turned back to the room temperature. After the reaction, an un-oxidized solid was got by extracting by using dichloromethane, ridding of water by using magnesium sulfate after gathering the organic layer, and purifying by the column chromatography. Then, the solid was dissolved in dichloromethane and hydrogen peroxide of 30% (1:1), and stirred for 24 hours. After the organic layer was extracted and gathered, it was dried by the rotary evaporator and further purified by the sublimator, thus obtaining the white product, yield of 60%.

Spectrum Data of the CPOC:

$^1$H NMR (400MHz, CDCl3, ppm): δ 8.137 (4H, d), 7.960~8.040 (4H, m), 7.840~7.940 (2H, m), 7.779 (4H, d), 7.603~7.656 (3H, m), 7.517 (4H, d), 7.424 (4, dd), 7.311 (4H, dd).

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A light-emission material, comprising a compound having Formula (I):

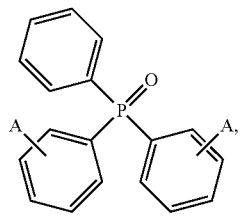

wherein each of A independently is:

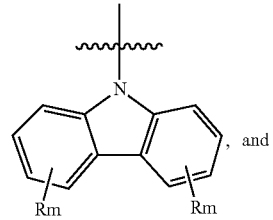

each of Rm independently is H, alkyl, alkenyl, alkynyl, CN, CF$_3$, alkylamino, amino, alkoxy, halo, aryl, or heteroaryl.

2. The light-emission material as claimed in claim 1, wherein A are the same.
3. The light-emission material as claimed in claim 1, wherein Rm are the same.
4. The light-emission material as claimed in claim 1, wherein the compound is:

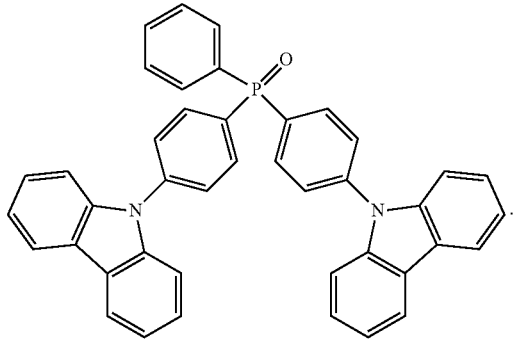

5. The light-emission material as claimed in claim 1, wherein the compound is:

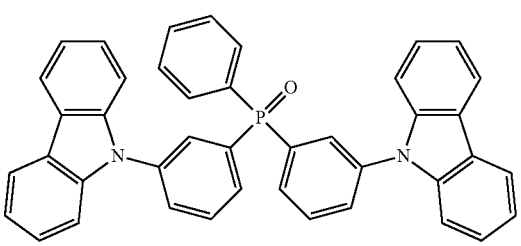

6. The light-emission material as claimed in claim 1, wherein the compound is:

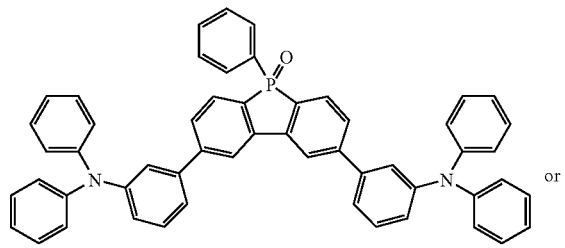

or

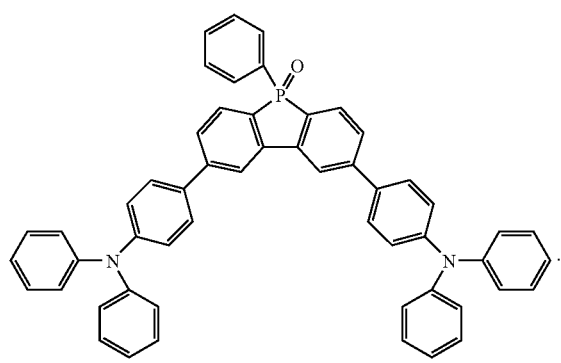

7. The light-emission material as claimed in claim 1, wherein the compound is:

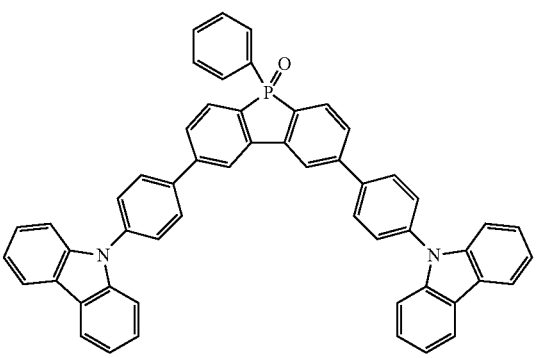

or

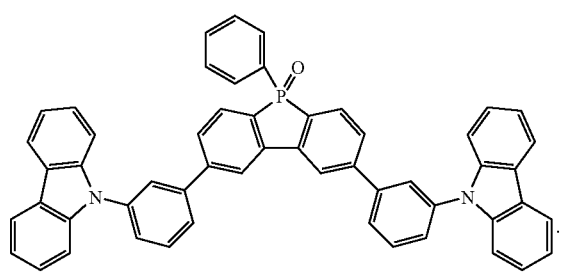

8. The light-emission material as claimed in claim 1, wherein the compound is:

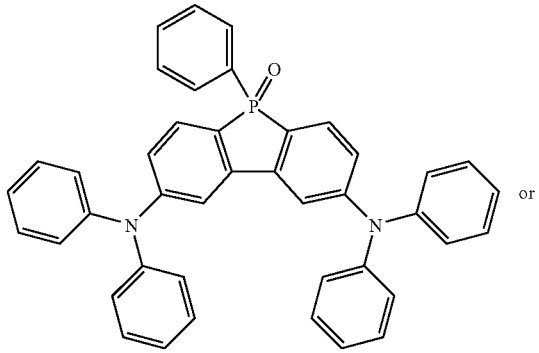

or

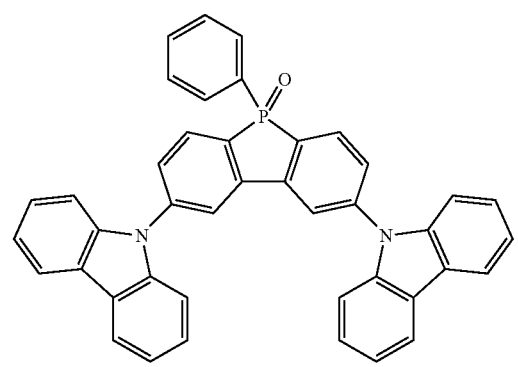

9. The light-emission material as claimed in claim 1, wherein the compound is:

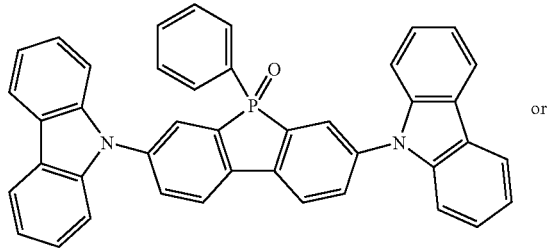

or

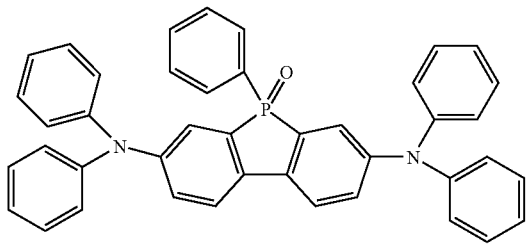

10. The light-emission material as claimed in claim 1, wherein the compound is used for a host light-emission material of an organic light-emitting diode.

11. An organic light-emitting diode, comprising:
a cathode and an anode; and
a light-emission layer including the light-emission material as claimed in claim 1 and disposed between the cathode and anode.

12. The organic light-emitting diode as claimed in claim 11, wherein the light-emission material further includes a dopant having Formula (II):

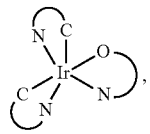

wherein each of

bidentate ligands independently is:

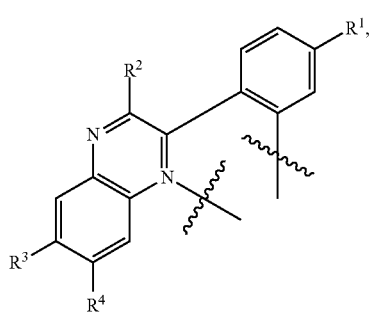

a

bidentate ligand is:

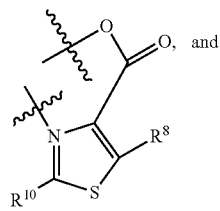

R1 to R10 each independently are H, alkyl, alkenyl, alkynyl, CN, CF3, alkylamino, amino, alkoxy, halo, aryl, or heteroaryl.

13. The organic light-emitting diode as claimed in claim 12, wherein R1 is H or F.

14. The organic light-emitting diode as claimed in claim 12, wherein R3 and R4 are the same.

15. The organic light-emitting diode as claimed in claim 12, wherein each of the

bidentate ligands is:

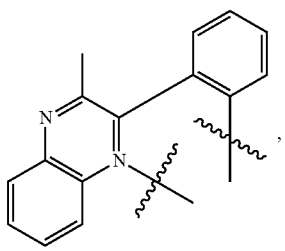

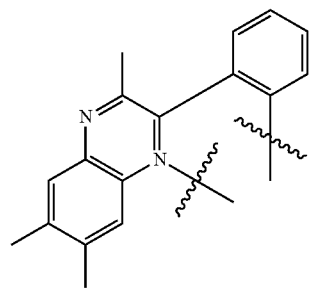

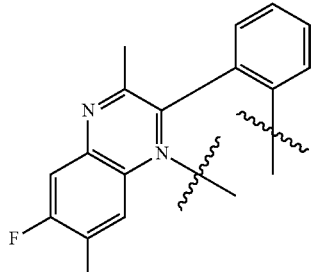

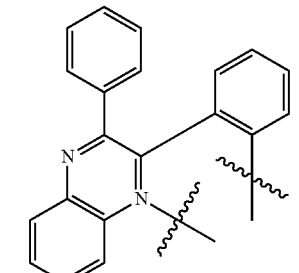

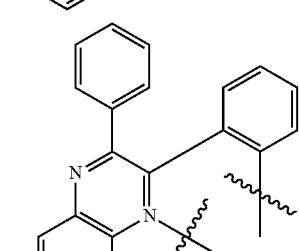

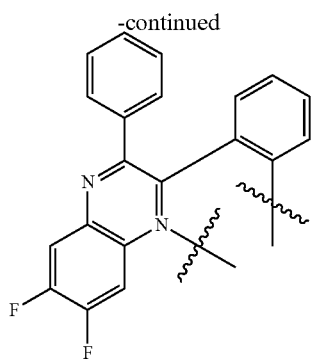
16. The organic light-emitting diode as claimed in claim 12, wherein each of the
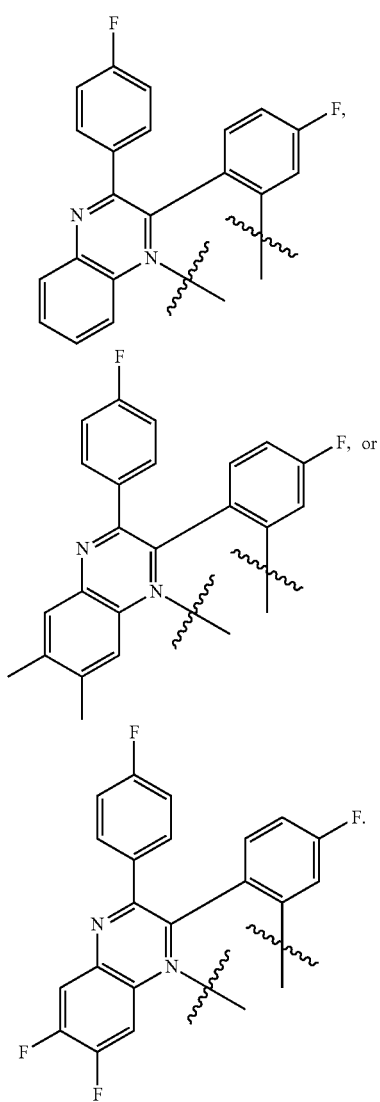
bidentate ligands is:
17. The organic light-emitting diode as claimed in claim 12, wherein the
bidentate ligand is:
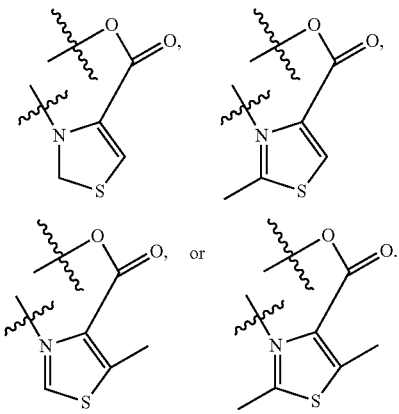
18. The organic light-emitting diode as claimed in claim 12, wherein the
bidentate ligand is:

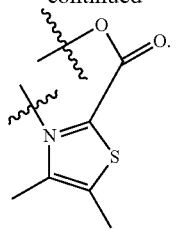
19. The organic light-emitting diode as claimed in claim 12, wherein the
bidentate ligand is:
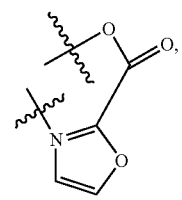 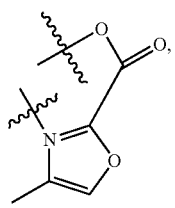 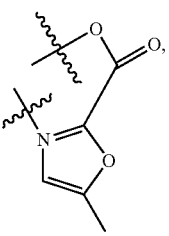
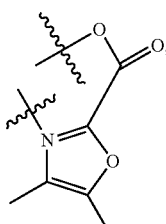 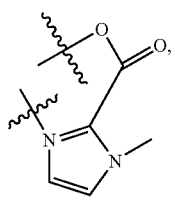
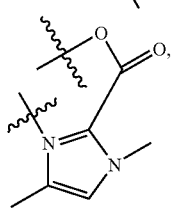 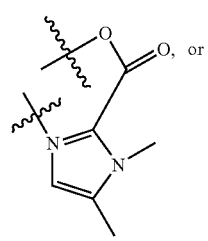
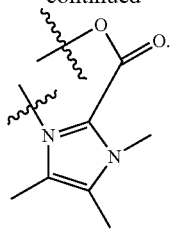
20. The organic light-emitting diode as claimed in claim 12, wherein the
bidentate ligand is:
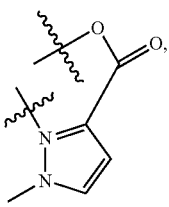 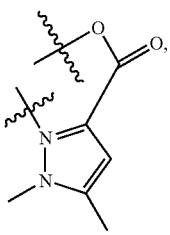
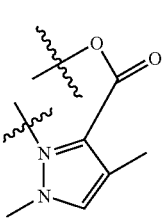 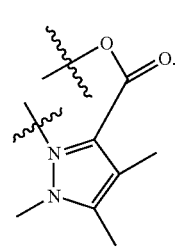
* * * * *